United States Patent [19]

Farine et al.

[11] 4,252,821

[45] Feb. 24, 1981

[54] METHOD FOR TREATING ULCERS

[75] Inventors: Jean-Claude Farine, Eysins; Adrian Schulthess, Begnins, both of Switzerland

[73] Assignee: Laboratoires OM Societe Anonyme, Geneva, Switzerland

[21] Appl. No.: 101,313

[22] Filed: Dec. 7, 1979

[51] Int. Cl.³ .......................................... A61K 31/205
[52] U.S. Cl. .................................................... 424/316
[58] Field of Search ......................................... 424/316

[56]     References Cited
       U.S. PATENT DOCUMENTS 4,038,390   7/1977   Esteve-Subirana ................. 424/316

Primary Examiner—Frederick E. Waddell
Attorney, Agent, or Firm—Ladas & Parry

[57]           ABSTRACT

Diethylamine persilate of formula

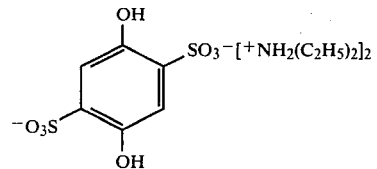

can be used against gastric and duodenal ulcers.

1 Claim, No Drawings

METHOD FOR TREATING ULCERS

The compound (bis-diethylamine)2,5-dihydroxybenzene-1,4-disulfonate of formula

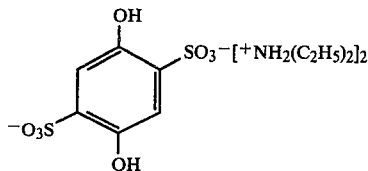

which has the generic international non-proprietary name bis-diethylamine salt of persilic acid or diethylamine persilate, is known to reduce the bleeding time of the rabbit ear in the test method according to Roskam (see U.S. Pat. No. 4,038,390).

It has now surprisingly been found that diethylamine persilate is useful in the treatment of gastric and duodenal ulcers.

In animal models, diethylamine persilate was found to have a protective effect against ulcers induced in male Wistar rats by different standard pharmacological methods, e.g. by acetylsalicyclic acid, by 4-butyl-1,2-diphenyl-pyrazolidine-3,5-dione, also known as phenylbutazone (INN) and by stress. Groups of 10 animals were used and the protective effect in the animals, treated by oral gavage, was demonstrated by a reduction of the ulcerogenic index. Diethylamine persilate was administered at a dosage level of 200 mg/kg/day. As reference compound NH-methyl-N'-cyano-N'[2-((4-methyl-5-imidazolyl)-methyl-thio)-ethyl]guanidine, also known as cimetidine (INN), was administered at a dosage level of 50 mg/kg/day. The results shown in table 1 represent the reduction of the ulcerogenic index as compared to a control group without treatment.

TABLE 1

|  | Ulcer induced by | | |
|---|---|---|---|
|  | Stress | Acetylsalicylic acid | Phenylbutazone |
| Diethylamine persilate | 85% | 91% | 99% |
| Cimetidine | 99% | 93% | 35% |

In another study, using groups of 10 female Wistar rats, the curative effect of diethylamine persilate and of cimetidine were determined by administering both compounds by oral gavage at the dosage level of 50 mg/kg/day after ulcers were induced by phenylbutazone. The curative effect of diethylamine persilate expressed as reduction of the ulcerogenic index as compared with an untreated control group was 37%. In this animal model, the curative effect of cimetidine was found to be 25%.

Two clinical investigations demonstrated the interest of diethylamine persilate in the treatment of ulcer disease in man.

In an open study, 20 patients suffering from gastric and duodenal ulcers were treated with an oral dose of 1,5 g of diethylamine persilate daily. The evaluation after 1 month treatment showed a rapid healing of the ulcers in 80% of the cases. No side effects have been observed.

In a double blind study, 40 patients suffering from proven peptic ulcer were treated during 1 month with either diethylamine persilate (1,5 g/day) or placebo. The results indicated in table 2 are based on endoscopic evaluation before and after treatment and show a significant difference in favour of diethylamine persilate.

TABLE 2

|  | No. of patients | Healed | Improved | Unchanged |
|---|---|---|---|---|
| Diethylamine persilate | 20 | 12 | 4 | 4 |
| Placebo | 20 | 3 | 4 | 13 |

The useful dosage range of diethylamine persilate in man is 0,1 g–5,0 g/day; the compound can be administered in any suitable galenic form, such as tablets, capsules, injectable solutions, suppositories, etc.

We claim:

1. A method for treating a human being or animal suffering from gastric or duodenal ulcer, comprising administering to said human being or animal a pharmaceutically active amount of the compound of formula

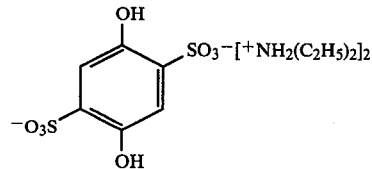

in a pharmaceutically acceptable carrier.

* * * * *